United States Patent
Lacey

(10) Patent No.: US 7,161,157 B2
(45) Date of Patent: Jan. 9, 2007

(54) SELF REGULATING DETECTOR RAIL HEATER FOR COMPUTED TOMOGRAPHY IMAGING SYSTEMS

(75) Inventor: Joe J. Lacey, Cambridge, WI (US)

(73) Assignee: General Electric Company, a New York Corporation, Schenectady, NY (US)

( * ) Notice: Subject to any disclaimer, the term of this patent is extended or adjusted under 35 U.S.C. 154(b) by 78 days.

(21) Appl. No.: 10/738,676

(22) Filed: Dec. 17, 2003

(65) Prior Publication Data

US 2005/0135553 A1 Jun. 23, 2005

(51) Int. Cl.
*G01T 1/24* (2006.01)
(52) U.S. Cl. .................................. 250/370.15; 378/19
(58) Field of Classification Search ........... 250/370.15, 250/370.09, 370.08; 378/4–20, 98.8
See application file for complete search history.

(56) References Cited

U.S. PATENT DOCUMENTS

| 5,103,092 A * | 4/1992 | Takahashi et al. | ........ 250/252.1 |
| 6,249,563 B1 * | 6/2001 | Snyder et al. | ................. 378/19 |
| 6,459,757 B1 * | 10/2002 | Lacey | ........................... 378/19 |
| 2003/0016779 A1 * | 1/2003 | Pohan et al. | .................. 378/19 |

* cited by examiner

*Primary Examiner*—Edward J. Glick
*Assistant Examiner*—Jurie Yun
(74) *Attorney, Agent, or Firm*—Henry Policinski; Joseph S. Heino; Patrick M. Bergin

(57) ABSTRACT

The present application discloses an x-ray detector for use in a computed tomography (CT) imaging system. The x-ray detector assembly comprises an array of detector cells coupled between detector rails. The present invention provides a self regulating heating element having a body that, when current is passed therethrough, radiates heat until a specific reference temperature is reached, at which point the resistance of the PTC heater increases, thus reducing the current through the PTC heater, and, as a result, the radiative heating of the PTC heater.

22 Claims, 3 Drawing Sheets

SELF REGULATING DETECTOR RAIL HEATER FOR COMPUTED TOMOGRAPHY IMAGING SYSTEMS

BACKGROUND OF THE INVENTION

The present invention relates generally to computed tomography (CT) imaging systems. More particularly, it relates to a method and apparatus for heating the detector rail of a CT imaging system.

In at least some CT imaging system configurations, a stationary floor-mounted frame includes an x-ray source and a radiation detector array. The x-ray source projects a fan-shaped beam that is collimated to lie within an X-Y plane of a Cartesian coordinate system and is generally referred to as the "imaging plane". The x-ray beam passes through the object being imaged, such as a patient. The beam, after being attenuated by the object, impinges upon the array of radiation detectors. The intensity of the attenuated beam radiation received at the detector array is dependent upon the attenuation of the x-ray beam of the object. Each detector element of the array produces a separate electrical signal that is a measurement of the beam attenuation at the detector location. The attenuation measurements from all the detectors are acquired separately to produce a transmission profile. The x-ray source and the detector array are rotated with a gantry within the imaging plane and around the object to be imaged. The X-ray source typically includes an x-ray tube that emits an x-ray beam. The X-ray detectors typically include a collimator for collimating x-ray beams received at the detector. A scintillator is located adjacent the collimator and photodiodes are positioned adjacent the scintillator.

In CT imaging, the gantry is used to rotate the x-ray source and the detector array around an object to be imaged so that the data corresponding to every angle is collected. Thereafter, the collected data is filtered, weighted, and typically is back projected by an image process to generate one or more diagnostic quality images.

In image reconstruction, it is assumed that the gain of each detector remains constant throughout a data acquisition process and that any change in x-ray signal intensity at the detector is due to patient anatomy. Unfortunately, this is not the case for several reasons. One particularly acute source of error in this regard has to do with how detector elements are affected by ambient conditions during operation. More specifically, detector element response to x-ray intensity varies as a function of temperature.

Also, temperature gradients along array rails and between rails have been known to change the relative positions of the rails. Even slight variations in the temperature of the detector rails can cause this misalignment. Obviously, if the detector elements are slightly misaligned, the resulting image will also be inaccurate.

There are other detector array components affected by changes of temperature. Specifically, the shunt resistance of a photo diode drops exponentially with temperature which results in leakage current and in general a decrease in the signal noise to ratio.

When array output varies as a function of element and array environment temperature, the quality of the resulting image is adversely affected. To this end, it has been observed that temperature effects on array output sometimes result in image artifacts that adversely affect the diagnostic usefulness of the resulting images.

There are many sources of heat in CT systems that directly affect the temperature of the array. Specifically, the x-ray tube used to generate the x-ray beam generates a large amount of heat in CT systems. In recent years, the problem has become more acute because of the desire to increase patient through-put. This has fueled the use of more powerful x-ray sources such that the amount of data required to generate images can be acquired in a shorter period of time. These high powered systems, while appreciably faster than their predecessors, have exacerbated the array heating problem and thus the associated image degradation.

In order to address temperature related array operation problems, prior devices have provided several heating systems to keep the array at an elevated, constant temperature. These heating systems are generally used to heat the elements to an expected temperature level and to maintain the temperature level throughout an acquisition. The CT imaging machine is then calibrated for optimum image of quality at the expected temperature.

Unfortunately, the array temperatures occurring in high power systems often exceed the temperature bound which renders the heating configurations ineffective in maintaining an isothermal condition. More simply, when detector temperature exceeds a target expected temperature level during some portion of an acquisition, the heating configuration which is limited by the upper temperature range is effectively useless.

Therefore, there remains a need for a simple and economic method for maintaining a detector array at a constant temperature, especially in conjunction with high-powered x-ray tubes.

BRIEF SUMMARY OF THE INVENTION

The present invention provides for a positive temperature coefficient (PTC) heater attached to the detector rail to heat the detector elements. The present invention may further provide for use of a PTC heater attached the detector module to directly heat the detector modules. Yet a further objective of the present invention is to employ a PTC heater that is self-regulating, i.e. it intrinsically maintains an isothermal condition. Yet a further object of the present invention is to provide a PTC heater which has no need of a traditional controller. In the event no PTC heater provides this element of self regulation, a controller may be used in conjunction with the present invention.

The foregoing and other features of the present invention will be apparent from the detailed description that follows.

DETAILED DESCRIPTION OF THE INVENTION

Figure 1:
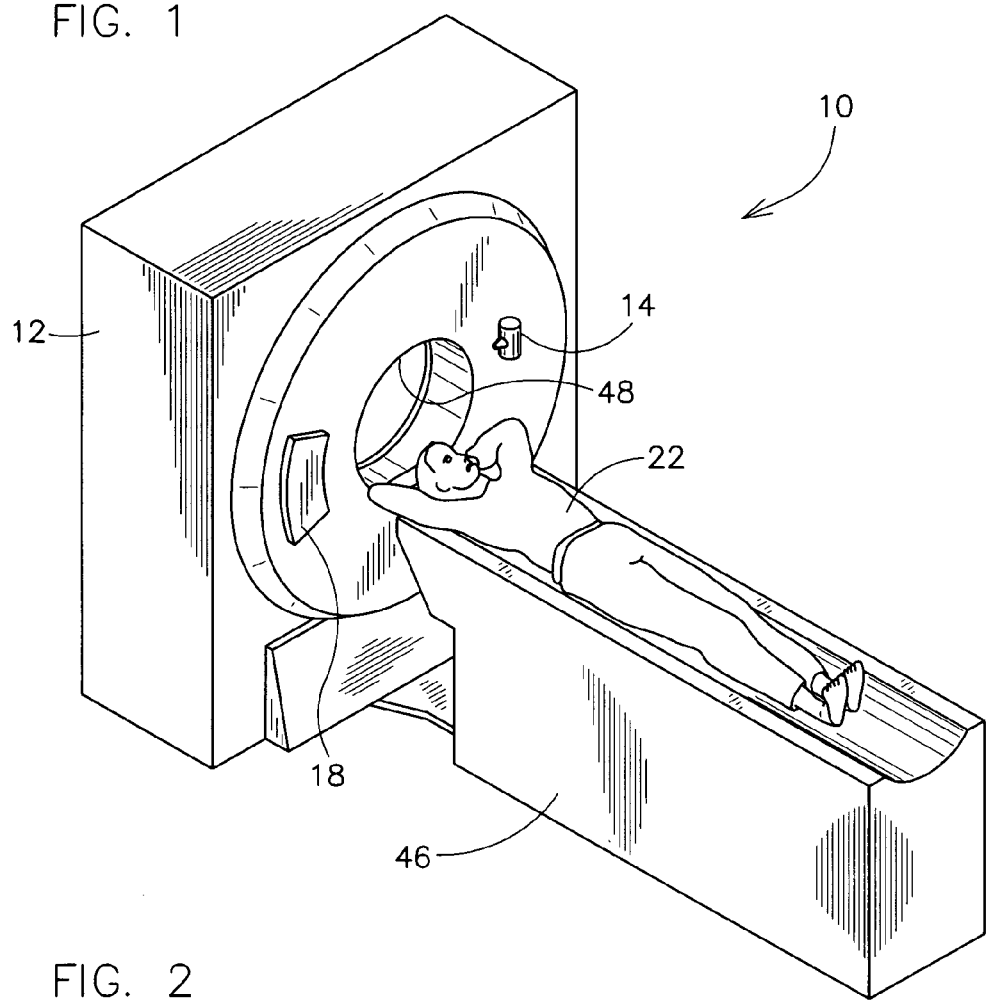
FIG. 1 is a pictorial view of a CT imaging system.
Figure 2:
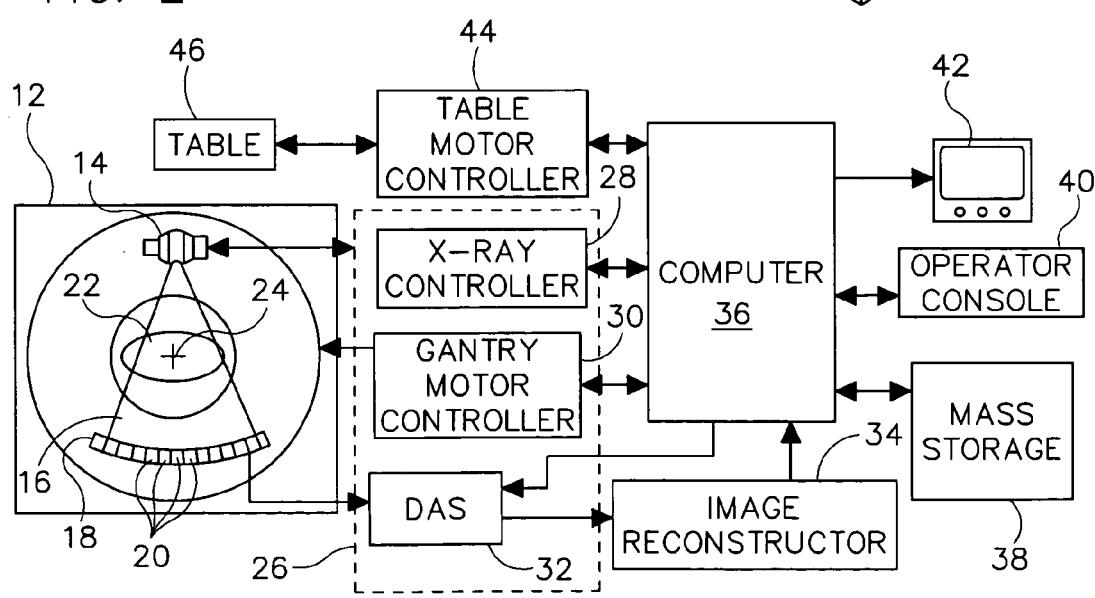
FIG. 2 is a block schematic of the system illustrated in FIG. 1.

Referring now to the drawings in detail wherein like-numbered elements correspond to like elements throughout, FIGS. 1 and 2 show a multi-slice scanning computed tomography (CT) imaging system 10. The CT imaging system 10 is shown as including a gantry 12 representative of a "third generation" CT imaging system. Gantry 12 has an X-ray source 14 that projects a beam of X-rays 16 toward a detector array 18 on the opposite side of gantry 12. Detector array 18 is formed by a plurality of detector rows (not shown) including a plurality of detector elements 20 which together sense the projected X-rays that pass through an object, such as a medical patient 22. Each detector element 20 produces an electrical signal that represents the intensity of an impinging X-ray beam and hence the attenuation of the beam as it passes through object or patient 22. During a scan to acquire X-ray projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 so that projection data corresponding to a plurality of quasi-parallel or parallel slices can be acquired simultaneously during a scan.

Rotation of gantry 12 and the operation of X-ray source 14 are governed by a control mechanism 26 of CT system 10. Control mechanism 26 includes an X-ray controller 28 that provides power and timing signals to X-ray source 14 and a gantry motor controller 30 that controls the rotational speed and position of gantry 12. A data acquisition system (DAS) 32 in control mechanism 26 samples analog data received from detector elements 20 through a flex cable (not shown in FIGS. 1 and 2), and converts the data to digital signals for subsequent processing. An image reconstructor 34 receives sampled and digitized X-ray data from DAS 32 and performs high-speed image reconstruction. The reconstructed image is applied as an input to a computer 36 which stores the image in a mass storage device 38.

Computer 36 also receives commands and scanning parameters from an operator via console 40 that includes at least one input device such as a keyboard or a mouse. An associated cathode ray tube display 42 allows the operator to observe the reconstructed image and other data from computer 36. The operator supplied commands and parameters are used by computer 36 to provide control signals and information to DAS 32, X-ray controller 28 and gantry motor controller 30. In addition, computer 36 operates a table motor controller 44 which controls a motorized table 46 to position patient 22 in gantry 12. Particularly, table 46 moves portions of patient 22 through the gantry opening 48.

In one embodiment, computer 36 includes a device, for example, a floppy disk drive or CD-ROM drive, for reading instructions and/or data from a computer-readable medium, such as a floppy disk or CD-ROM. In another embodiment, computer 36 executes instructions stored in firmware (not shown). Computer 36 is programmed to perform functions described herein, accordingly, as used herein, the term "computer" is not limited to just those integrated circuits typically referred to in the art as computers, but more broadly refers to computers, processors, microcontrollers, microcomputers, programmable logic controllers, application specific integrated circuits, and other programmable circuits.

Figure 3:
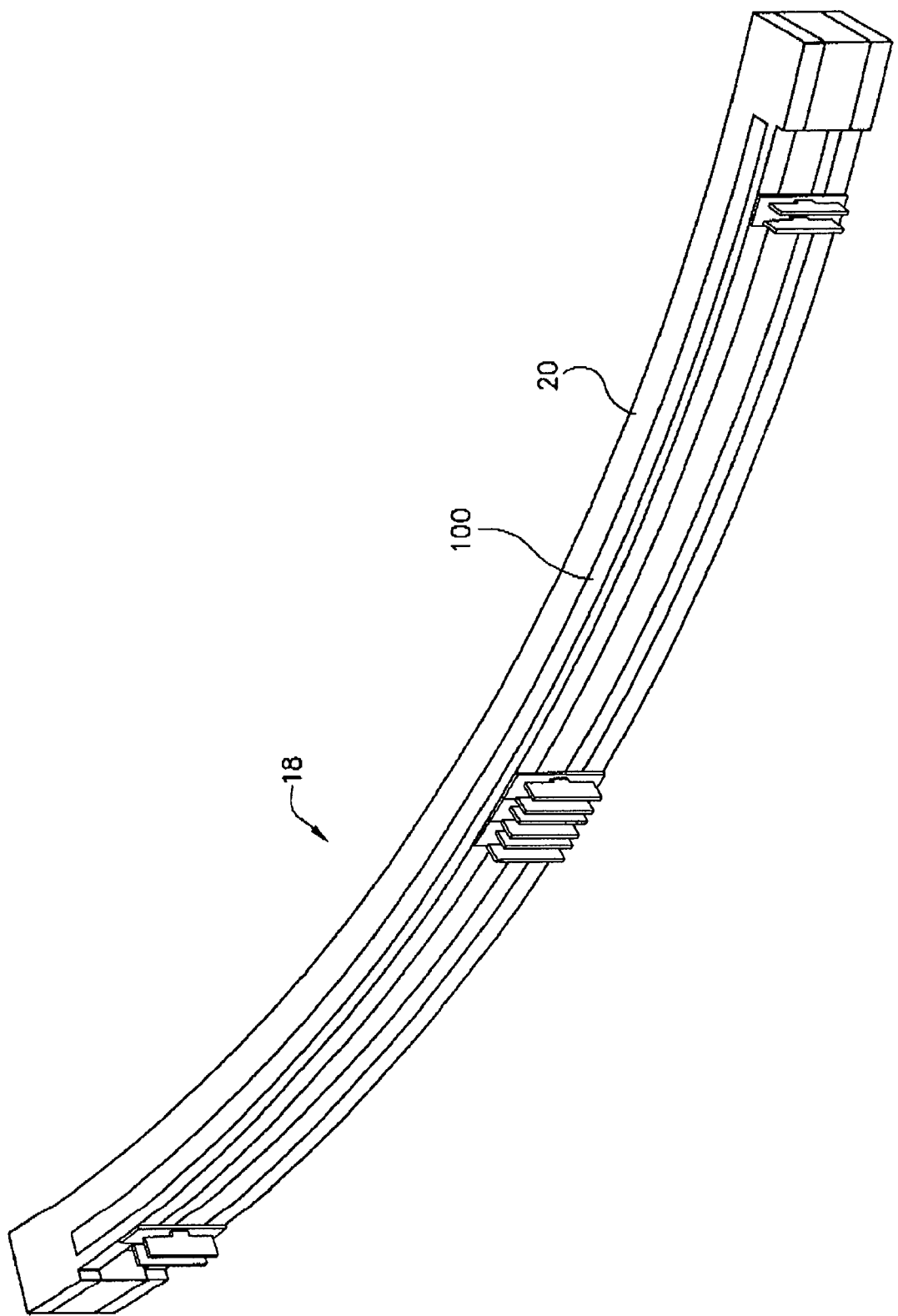
FIG. 3 is a front cross-sectional schematic view of the detector array of the present invention having a PTC heater.
Figure 4:
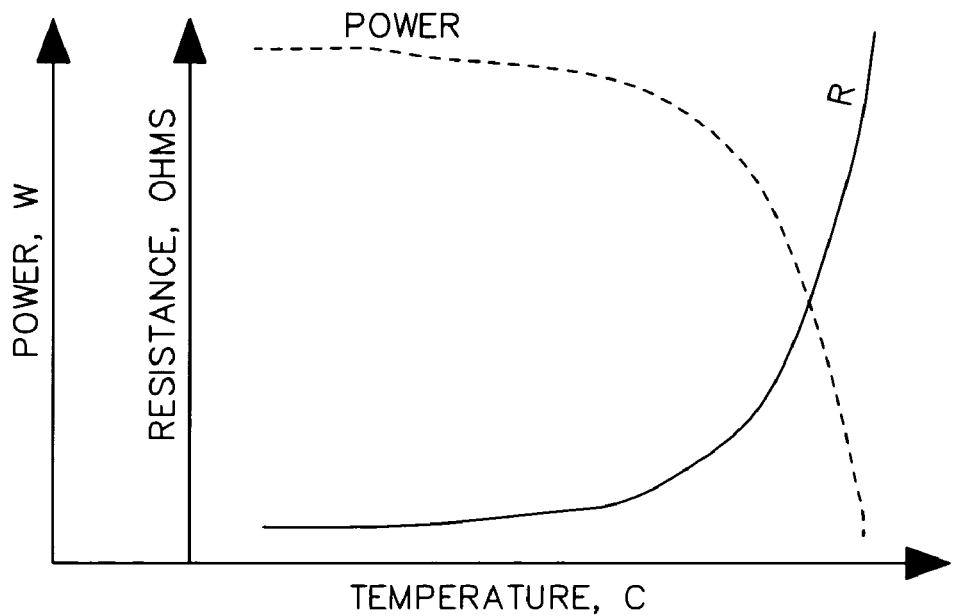
FIG. 4 is a graph showing the relationship between the power output of the PTC heater and the resistance of the PTC heater.

As shown on FIG. 3, the PTC heater 100 is a strip attached to the outside of the detector array 18. PTC heaters 100 are, in general, doped polycrystalline ceramic having a large percentage of barium titanate. In the operating range of the PTC heater 100, resistance increases rapidly with temperature, as shown in FIG. 4. As resistance increases, current and/or voltage across the PTC heater 100 drops, reducing the amount of heat radiated by the body of the PTC heater 100. The temperature at which a PTC heater 100 begins to limit itself is called its reference temperature.

Therefore, in the event that an existing PTC heater 100 is not achieving the target temperature, the heater can be replaced with a PTC heater 100 having a larger heating element body, which increases the amount of power through the body of the heater element. Because the PTC heater 100 is self regulating, normal controls, as might be found on prior devices, can be eliminated as long as the heating element can respond to all heating conditions within its dynamic range in order to maintain the target temperature within the accepted tolerances.

Figure 5A:
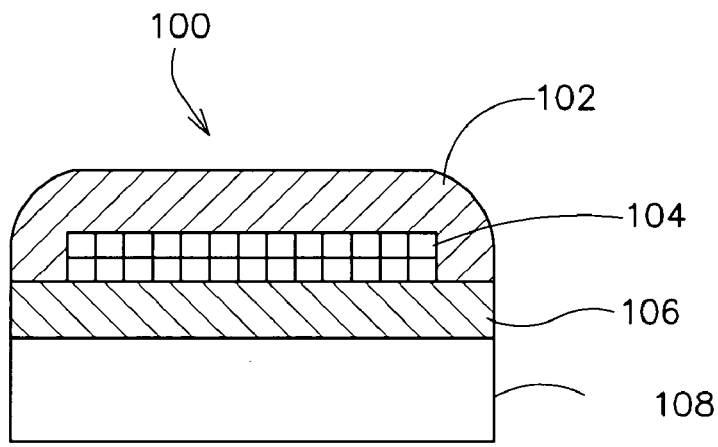
FIG. 5A is an elevational cross-sectional view of one type of PTC heater.
Figure 5B:
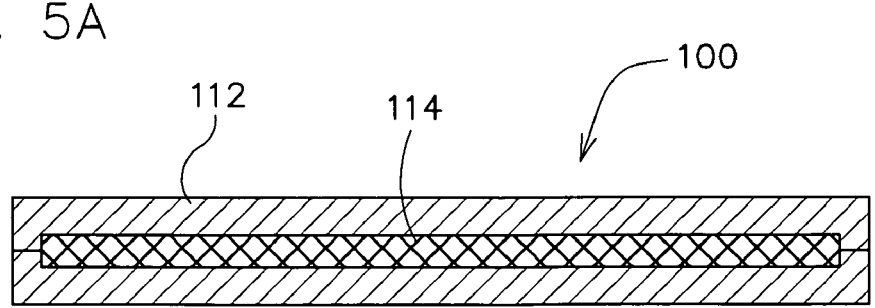
FIG. 5B is an elevational cross-sectional view of another type of PTC heater.

In general, PTC heating elements 100 are small ceramic stones and have fast heating response times and plateau when their predefined reference temperature is reached. The stones can be shaped in any number of configurations including, but not limited to, a square, rectangular, round, ring or donut shape. In general, existing PTC heaters 100 are either made as solid ceramic bars as shown in FIG. 5A or using Thick Film Technology (TFT) as shown in FIG. 5B. As shown in FIG. 5A, the PTC heater 100 is comprised of a first dielectric area 102, a heater layer 104, a second dielectric area 106 and a substrate 108. When constructed using TFT, the heater may include a Kapton insulator 112 surrounding a PTC printed resistive circuit 114. Using TFT, the PTC heater 100 can either be applied directly to a substrate or to a flexible sheet.

The detector temperature control system can consist of either a single continuous PTC heater element 100 or a plurality of segments of PTC heater elements 100 attached along the detector rails 20 and/or detector modules to effect heating of the detector array 18. A study can be made of PTC heaters 100 such that one can identify the proper resistance curve and develop a heating system that intrinsically seeks to maintain an isothermal condition. The design can be used without a traditional controller as the nature of a PTC heater 100 is that it is self-regulating. If the self-regulation is not precise enough, a controller in the form of a current, voltage or heater resistance sensor can be placed into the electrical circuit and calibrated to provide a control function.

In summary, the present invention provides for a detector assembly for use in a computed tomography (CT) imaging system comprised of a detector array; and a self regulating heating element. The self regulating heating element radiates heat until it reaches a specific reference temperature at which point the resistance of the self regulating heater element increases, thus reducing the current through the self regulating heater element, and in turn the radiative heating of the self regulating heater element. The self regulating heating element could be a single PTC heater. The self regulating heater could also have several segments covering portions of the detector array. The present invention also provides a method for maintaining an x-ray detector ray in isothermal condition comprising the steps of coupling a self regulating heating element through the detector array and providing a variable current or voltage source to said heating element.

The foregoing description has been presented for purposes of illustration. It is to be understood that widely different embodiments of the invention may be constructed without departing from the spirit and the scope of the present invention. It should also be understood that the present invention is not limited to the specific embodiments described in the specification, except as defined in the appended claims.

What is claimed is:

1. A detector assembly for use in a computed tomography (CT) imaging system comprising:
 a detector array; and
 a self regulating heating element in direct contact with the detector array.

2. The detector assembly of claim 1 wherein said self regulating heating element radiates heat until it reaches a specific reference temperature at which point the resistance of the self regulating heating element increases and current through the self regulating heating element decreases, thereby reducing the radiative heating by the self regulating heating element.

3. The detector assembly of claim 1 wherein said self regulating heating element is a PTC heater.

4. The detector assembly of claim 3 wherein said self regulating heater has multiple segments.

5. A detector assembly for use in a computed tomography (CT) imaging system comprising:
 a detector array having a plurality of detector modules; and
 a plurality of self regulating heating elements in direct contact with the detector modules.

6. The detector assembly of claim 5 wherein said self regulating heating element radiates heat until it reaches a specific reference temperature at which point the resistance of the self regulating heating element increases and current through the self regulating heating element decreases, thereby reducing the radiative heating by the self regulating heating element.

7. The detector assembly of claim 5 wherein said self regulating heating element is a PTC heater.

8. The detector assembly of claim 7 wherein said self regulating heater has multiple segments.

9. A detector assembly for use in a computed tomography (CT) imaging system comprising:
 a detector array; and
 a self regulating heating element in direct contact with the detector array, said heating element having a body that, when current is passed therethrough, radiates heat until a specific reference temperature is reached, at which point the resistance of the self regulating heating element increases and current through the self regulating heating element decreases, thereby reducing the radiative heating by the self regulating heating element.

10. The detector assembly of claim 9 wherein said self regulating heating element is a PTC heater.

11. The detector assembly of claim 10 wherein the PTC heater has multiple segments.

12. A detector assembly for use in a computed tomography (CT) imaging system comprising:
 a detector array; and
 a self-regulating PTC heater in direct physical and thermal contact with said detector array.

13. A detector assembly for use in a computed tomography (CT) imaging system comprising:
 a detector array having a plurality of detector modules; and
 a plurality of self-regulating PTC heating elements attached to said, the PTC heating elements being in direct physical contact with the detector modules.

14. A detector assembly for use in a computed tomography (CT) imaging system comprising:
 a detector array; and
 a multi-segmented self-regulating PTC heater in direct contact with said detector array.

15. A method for maintaining an x-ray detector array in isothermal condition comprising:
 coupling a self regulating heating element through the detector array, the self-regulating heating element being in direct physical contact with the detector array; and
 providing a variable current/voltage source to said heating element.

16. The method of claim 15 wherein said self regulating heating element increases its resistance with temperature.

17. The method of claim 16 wherein said self regulating heating element permits less current/voltage to pass therethrough when it reaches a specified temperature and thereby radiates less heat.

18. The method of claim 17 wherein said self regulating heating element is employed to maintain the detector array in an isothermal condition.

19. A method for maintaining the detector modules of an x-ray detector array in isothermal condition comprising:
 providing a self regulating heating element in direct physical contact with the detector modules; and
 providing a variable current/voltage source to said heating element.

20. The method of claim 19 wherein said self regulating heating element increases its resistance with temperature.

21. The method of claim 20 wherein said self regulating heating element permits less current/voltage to pass therethrough when it reaches a specified temperature and thereby radiates less heat.

22. The method of claim 21 wherein said self regulating heating element is employed to maintain the detector modules in the detector array in an isothermal condition.

* * * * *